United States Patent
Wilkerson

(10) Patent No.: US 8,202,239 B2
(45) Date of Patent: Jun. 19, 2012

(54) ANKLE DEROTATION AND SUBTALAR STABILIZATION ORTHOSIS

(76) Inventor: Gary Blaine Wilkerson, Signal Mountain, TN (US)

(*) Notice: Subject to any disclaimer, the term of this patent is extended or adjusted under 35 U.S.C. 154(b) by 699 days.

(21) Appl. No.: 11/858,204

(22) Filed: Sep. 20, 2007

(65) Prior Publication Data
US 2008/0082034 A1 Apr. 3, 2008

Related U.S. Application Data

(60) Provisional application No. 60/846,738, filed on Sep. 25, 2006.

(51) Int. Cl.
*A61F 5/00* (2006.01)
(52) U.S. Cl. .......... 602/27; 602/16; 602/23; 602/65
(58) Field of Classification Search ............. 602/16, 602/28, 29, 23, 27, 60–62, 65; 128/882, 128/869; D24/191–192
See application file for complete search history.

(56) References Cited

U.S. PATENT DOCUMENTS

| | | | | |
|---|---|---|---|---|
| 4,556,054 A | * | 12/1985 | Paulseth | 602/27 |
| 5,902,259 A | * | 5/1999 | Wilkerson | 602/27 |
| 6,689,081 B2 | * | 2/2004 | Bowman | 602/27 |

* cited by examiner

*Primary Examiner* — Patricia Bianco
*Assistant Examiner* — Keri J Nelson
(74) *Attorney, Agent, or Firm* — Chambliss, Bahner & Stophel, P.C.

(57) ABSTRACT

The invention is an ankle derotation and subtalar stabilization system that incorporates a pivoting adjustable-tension oblique tether strap that is anchored to both a forefoot component and leg component, and that is contiguous with pivoting adjustable-tension derotation strap that passes behind the leg and that is secured to a leg component. The system restrains oppositely directed rotation between the foot and the leg, and can actually after the normal biochemical relationship in a manner that produces foot rotation in a direction opposite to that which is normally coupled with leg rotation, without restriction of upward and downward foot movement. The primary application for the system is restraint of excessive subtalar joint inversion, leg external rotation, and anterolateral rotary displacement of the talus, but it can also be configured to restrain subtalar eversion and leg internal rotation through its incorporation into the structure of an ankle orthosis or shoe.

21 Claims, 18 Drawing Sheets

ANKLE DEROTATION AND SUBTALAR STABILIZATION ORTHOSIS

CROSS REFERENCE TO RELATED APPLICATIONS

This application claims benefit of Provisional application Ser. No. 60/846/738 filed Sep. 25, 2006.

REFERENCES CITED

U.S. PATENT DOCUMENTS

| | | | |
|---|---|---|---|
| 4,237,874 | December 1980 | Nelson | 128/80 H |
| 4,441,265 | April 1984 | Burns et al. | 36/117 |
| 4,646,726 | March 1987 | Westin et al. | 128/80 H |
| 4,753,229 | January 1988 | Sutherland | 128/80 H |
| 4,982,733 | January 1991 | Broadhurst et al. | 128/804 |
| 5,031,607 | July 1991 | Peters | 128/60 H |
| 5,067,486 | November 1991 | Hely | 128/80 H |
| 5,209,722 | May 1993 | Miklaus et al. | 602/27 |
| Des 338,066 | August 1993 | Baron | D24/192 |
| 5,472,411 | December 1995 | Montag, et al. | 602/23 |
| 5,810,754 | September 1998 | Kenosh | 602/27 |
| 5,899,872 | May 1999 | Gilmour | 602/65 |
| 5,944,678 | August 1999 | Hubbard | 602/27 |
| 5,971,946 | October 1999 | Quinn et al. | 602/27 |
| 6,053,884 | April 2000 | Peters | 602/27 |
| 6,056,713 | May 2000 | Hayashi | 602/27 |
| 6,228,043 B1 | May 2001 | Townsend et al. | 602/27 |
| 6,602,215 B1 | August 2003 | Richie, Jr. | 602/27 |
| 6,793,640 B1 | September 2004 | Avon | 602/23 |
| 6,689,081 B2 | February 2004 | Bowman | 602/27 |

OTHER PUBLICATIONS

Wilkerson G B, Kovaleski J E, Meyer M A. Stawitz C E. Effects of the subtalar sling ankle taping technique on combined talocrural-subtalar motions. *Foot and Ankle International*, 26(3):239-246, 2005.

Wilkerson G B. Biomechanical and neuromuscular effects of ankle taping and bracing. *Journal of Athletic Training*, 37(4):436-445, 2002.

STATEMENT REGARDING FEDERALLY SPONSORED RESEARCH OR DEVELOPMENT

Not applicable.

BACKGROUND OF THE INVENTION

The invention relates to control of excessive and abnormal displacements of the talocrural and subtalar joints of the ankle during physical activity, for the purposes of prevention of injury, protection of previously injured ligaments, or compensation for chronic instability.

An exceedingly wide variety of ankle orthosis designs have been developed, which have different closure mechanisms, strap configurations, and material characteristics. Prior art has recognized that restraint of abnormal ankle displacement requires orthosis elements that are firmly secured to both the leg and the foot, but the none of the linkage mechanisms between the leg and the foot segments described in the prior art effectively restrain excessive subtalar joint motion or combined rotary and translational displacement of talus, while simultaneously permitting unrestrained upward and downward movement of the foot in the sagittal plane. A review of the biomechanical function of the leg, ankle, and foot is essential for understanding of the mechanism by which a new and original pivoting strap system design provides an optimal level of ankle stability when incorporated into the structure of an ankle orthosis or shoe.

Movements of body segments have traditionally been defined by assuming that the proximal segment (closest to the body torso) remains stationary, while the non-weightbearing distal segment (furthest from the body torso) changes its position in space. The movements of the distal segment are defined in terms of cardinal planes, which correspond to the three dimensions of space and are perpendicular to one another. Isolated upward and downward movements of the foot in the sagittal plane (respectively termed dorsiflexion and plantar flexion) are associated with rotation around a horizontal axis that is perpendicular to the long axis of the foot. Isolated inward and outward tilting movements of the sole of the foot in the frontal plane (respectively termed supination and pronation) are associated with rotation around a horizontal axis that is aligned with the long axis of the foot. Isolated inward and outward displacements of the long axis of the foot in the transverse plane (respectively termed adduction and abduction) are associated with rotation around a vertical axis that is aligned with the long axis of the stationary leg.

Although the ankle is widely viewed as a single joint between the leg and foot, ankle motion actually involves extremely complex interrelationships between the articular surfaces and ligaments of the talocrural joint, subtalar joint, transverse tarsal joint, tarsometatarsal joints, and metatarsophalangeal joints. The motions of an individual joint, which are almost never confined to a single cardinal plane, are primarily determined by the geometric configuration of its articular surfaces. A joint's "functional" axis of rotation is an imaginary line in space, around which angular motion occurs. Thus, the "functional" axis of angular motion for a given joint has a spatial orientation that typically deviates to some degree from vertical and horizontal reference planes.

The talocrural joint (TCJ), which is comprised of the tibia, fibula, and talus, is widely referred to as the ankle joint. Most of the upward and downward movement of the foot results from TCJ motion, but most of the side-to-side movement of the foot results from motion between the talus and calcaneus in the subtalar joint (STJ). Although the TCJ and STJ function in a highly integrated manner, they represent two distinctly separate joints. Thus, the TCJ should be viewed as the "upper" ankle joint and the STJ as the "lower" ankle joint. The orientation of the functional axis of the TCJ closely corresponds to the lower tips of the bony protuberances on either side of the ankle (the tibial malleolus and the fibular malleolus). Although TCJ motion primarily occurs within the sagittal plane, and is referred to as dorsiflexion and plantar flexion, the TCJ functional axis has a somewhat oblique orientation that combines some degree of supination and adduction with plantar flexion, and some degree of pronation and abduction with dorsiflexion (FIGS. 1-4).

The inward rotation of the sole of the foot that results from STJ motion is referred to as inversion, whereas the reciprocal outward rotation is referred to as eversion. From an outer side view, the average inclination of the STJ functional axis relative to the sole of the foot approximates a 45-degree orientation (FIG. 5). The function of the STJ has been compared to that of a "mitered hinge" between the leg and the foot, which produces rotation of the segments on either side of the hinge in opposite directions (FIG. 6). During weightbearing, frictional force between the ground and the foot results in the transfer of torque to the leg. The "mitered hinge" effect of the STJ causes inversion to be coupled with external rotation of the leg, and causes eversion to be coupled with internal rotation of the leg (FIG. 7). Similarly, rotation of the leg upon a weightbearing foot results in the transfer of torque through the STJ to the forefoot.

Excessive inversion torque is the dominant injury producing force in 85% of all ankle sprains. The position of the foot at the moment of injury is typically a combination of plantar flexion and inversion. The anterior talofibular ligament (ATFL) is the weakest and most vulnerable component of the lateral ligament complex, and it is the first to be stressed by the typical ankle sprain mechanism. Numerous experts in ankle biomechanics have emphasized the importance leg external rotation as key factor contributing to disruption of the ATFL. If the foot is firmly fixed to the ground, such that there is minimal movement at the ground-sole interface, torque is concentrated on the linkage between the foot and leg. As the leg rotates externally upon the talus, the ATFL is subjected to tensile stress. Tearing and/or chronic elongation of the ATFL results in abnormal rotary mobility within the TCJ (anterolateral rotary instability: anterior translation of the anterolateral portion of the talus from the tibio-fibular socket as the leg rotates externally; FIG. 8).

To effectively prevent lateral ankle sprain, or chronic rotary displacement, an ankle orthosis must restrain excessive and abnormal coupled motions within the joints of the forefoot (tarsometatarsal joints and transverse tarsal joint) and hindfoot (STJ and TCJ). To be practical for use among athletes, the device must not significantly restrict upward and downward foot movements necessary for running and jumping (dorsiflexion and plantar flexion). The degree of resistance provided to a given ankle motion by a orthosis is determined by the following factors: 1) the geometric configuration of the elements of the device relative to the spatial orientation of the functional axis of motion, 2) the degree of stiffness or elasticity of the materials that comprise the orthosis elements, and 3) the degree of fixation of the device to both the leg and the foot segments.

When subjected to excessive inversion stress, the articular surfaces of the joints of the foot and ankle are distracted laterally and compressed medially. Several different strategies may be employed to resist such joint displacement. A "stirrup brace" incorporates medial and lateral components that are constructed from a relatively rigid plastic. Both components contribute to ankle stability, but have different biomechanical effects. The component that spans the medial joint surfaces acts like a "spacer bar" to resist medial compression. Assuming that the lateral component of a stirrup brace exerts pressure against the lateral surface of the ankle, it acts as a "buttress" to resist lateral distraction. Cloth adhesive tape applied to the ankle provides support through a different mechanism. When skillfully applied, strips of adhesive tape develop tension in response to distraction of the joints that they span, thereby acting like a "tether" that resists separation of its attachment points. Thus, tape may function like an "external ligament" that limits the displacement of underlying joint surfaces. Lace-up ankle braces, which are constructed from pliable fabric (e.g., nylon or vinyl) and are secured to the leg and foot segments by means of a system of eyelets and lacing (Hely, U.S. Pat. No. 5,067,486; Nelson, U.S. Pat. No. 4,237,874), do not conform to the ankle contours as closely as adhesive tape. The primary mode of protection for the lateral ankle ligaments provided by a lace-up ankle brace is probably derived from the manner in which the joints of the hindfoot are encased by material (i.e., a lateral buttress effect).

Ideally, an ankle support system should restrict excessive motion within the STJ, without significant restriction of motion within the TCJ. Because a wide range of upward and downward foot motion is clearly desirable for activities that involve running and jumping, some semi-rigid ankle brace designs have incorporated hinges on the medial and/or lateral aspects of the brace that are intentionally aligned with the approximate location of the TCJ axis (Bowman, U.S. Pat. No. 6,689,081; Miklaus et al., U.S. Pat. No. 5,209,722; Peters, U.S. Pat. No. 5,031,607; Peters, U.S. Pat. No. 6,053,884; Quinn et al., U.S. Pat. No. 5,971,946; Richie Jr., U.S. Pat. No. 6,602,215; Westin et al., U.S. Pat. No. 4,646,726). Fixation of brace components to the leg and foot segments is often provided by straps that incorporate Velcro hook and loop closure material. Many ankle braces incorporating adjustable-tension straps that link foot and leg components include a semi-rigid cuff and strap system that encircles the leg (Broadhurst, U.S. Pat. No. 4,982,733; Gilmour, U.S. Pat. No. 5,899,872; Hayashi, U.S. Pat. No. 6,056,713; Kenosh, U.S. Pat. No. 5,810,754; Peters, U.S. Pat. No. 6,053,884; Sutherland, U.S. Pat. No. 4,753,229; Westin et al., U.S. Pat. No. 4,646,726). To reduce interference with normal upward and downward movement of the foot, adjustable-tension straps are sometimes anchored to foot and/or leg brace components by means of a pivoting connection (Avon, U.S. Pat. No. 6,793,640; Baron, Des. 338,066; Bowman, U.S. Pat. No. 6,689,081; Montag, U.S. Pat. No. 5,472,411; Richie Jr., U.S. Pat. No. 6,602,215; Sutherland, U.S. Pat. No. 4,753,229; Westin et al., U.S. Pat. No. 4,646,726). An ankle support device is typically separate from the structure of the shoe within which it is worn, but support ankle systems may be embodied in either the form of an orthosis or incorporated into the structure of a shoe (Burns, U.S. Pat. No. 4,441,265; Kenosh, U.S. Pat. No. 5,810,754; Sutherland, U.S. Pat. No. 4,753,229; Townsend et al., U.S. Pat. No. 6,228,043).

Because motion of the talus is influenced by torque that is transferred from joints in the forefoot, restriction of excessive forefoot inversion is essential for optimal maintenance ankle stability. To control forefoot inversion, the support system must span the set of articulations between the talus, calcaneus, navicular, cuboid, and fifth ray, and it must be firmly anchored to both the leg and forefoot. The designs of most ankle support systems reflect a focus on enhancement of the stability of the hindfoot, without any attempt to control motion within the joints of the forefoot. However, there are a few notable exceptions. Westin et al. (U.S. Pat. No. 4,646,726) disclosed a design that incorporates an adjustable-tension oblique strap, which extends from the forefoot portion of a footplate component to a common junction with another vertical strap that is anchored to a leg cuff component. Kenosh (U.S. Pat. No. 5,810,754) disclosed a non-adjustable design that incorporates a "talofibular support portion" that is continuous in structure with the rest of the orthotic, which is clearly intended to provide a forefoot stabilization effect. Avon (U.S. Pat. No. 6,793,640) disclosed a device that is intended for control of ankle instability associated with paralysis, which incorporates a pair of obliquely-oriented adjustable straps on its medial and lateral aspects that span the joints of the forefoot and midfoot.

BRIEF SUMMARY OF THE INVENTION

An ankle taping procedure that incorporates tape strips applied in such a manner that their orientation is perpendicular to the orientation of the STJ axis has been shown to be highly effective in restricting inversion and translatory movement of the foot in relation to the leg (FIG. 9). Because the tape strips are anchored to the undersurface of the forefoot, span the joints of the forefoot and midfoot on the lateral aspect, and wrap around the leg in a posterior to medial direction, they have the effect of restraining subtalar inversion and anterolateral rotary displacement of the talus when the leg is externally rotated. Adustable-tension brace straps that originate on the lateral aspect of the ankle, wrap around the posterior and medial aspects of the leg, and anchor to a leg component have been previously disclosed (Bowman, U.S. Pat. No. 6,689,081; Broadhurst, U.S. Pat. No. 4,982,733; Hubbard, U.S. Pat. No. 5,944,678; Sutherland, U.S. Pat. No. 4,753,229), but none of them have originated from the lateral forefoot area. The present invention is an ankle derotation and subtalar stabilization system that incorporates a pivoting adjustable-tension oblique tether strap that is anchored to the forefoot and a contiguous pivoting adjustable-tension derotation strap that passes behind the leg.

DETAILED DESCRIPTION OF THE INVENTION

None of the prior art has disclosed an adjustable-tension tether strap that is anchored to the forefoot portion of a foot cuff/orthotic component, that pivots in a manner to permit normal upward and downward movement of the foot, and that is contiguous with a adjustable-tension derotation strap that wraps behind the leg and anchors to a leg cuff component. Because the major portion of forefoot motion results from rotation around the functional axis of the STJ, optimal resistance to excessive forefoot motion can be accomplished through a design that generates tensile resistance in a plane that is perpendicular to that of the STJ axis. Such a system requires moveable elements for the following reasons: 1) plantar flexion and dorsiflexion would be greatly limited by a non-elastic or non-articulated device that connects the leg and the forefoot, and 2) the orientation of the subtalar axis changes when the foot is dorsiflexed and plantar flexed.

Figure 1:
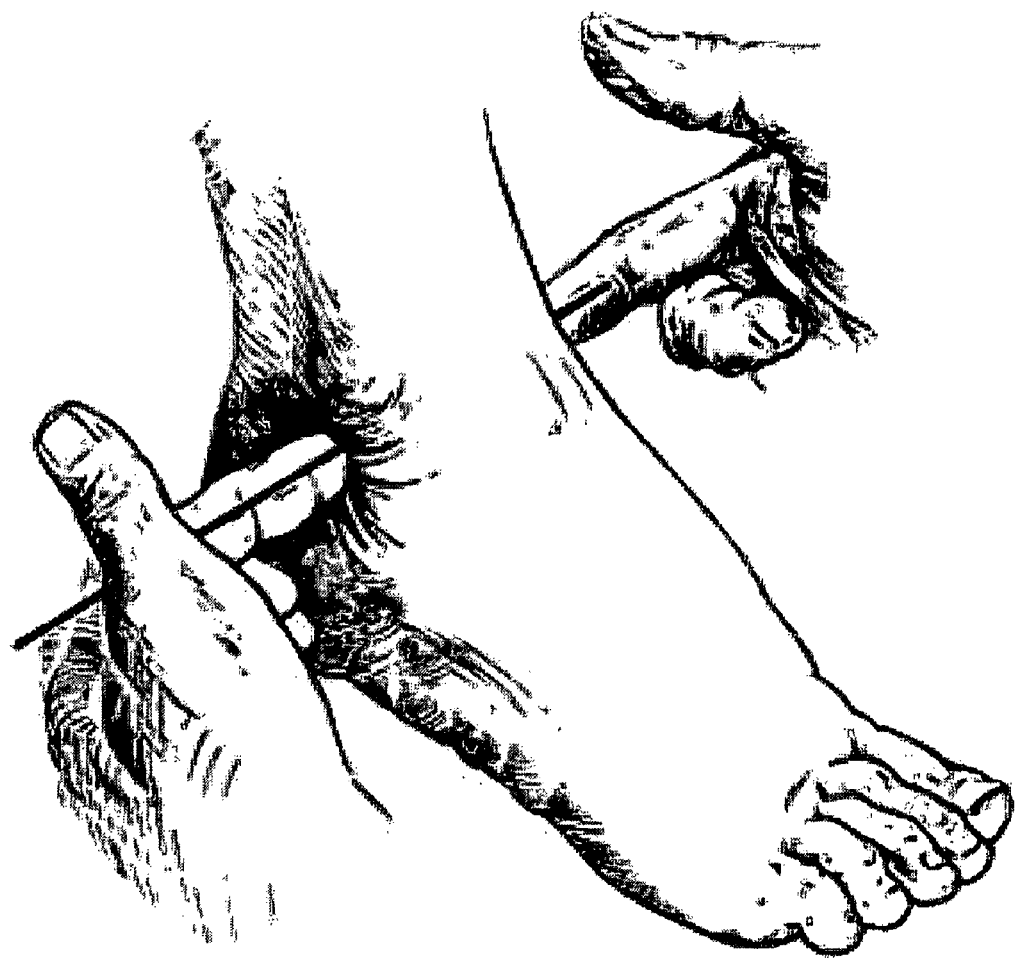
FIG. 1 is a depiction of the approximate orientation of the functional axis of rotation of the talocrural joint (TCJ), which roughly intersects the lowermost portions of the bony protuberances on the medial (inner) and lateral (outer) aspects of the ankle (i.e., the tibial malleolus and the fibular malleolus).
Figure 2:
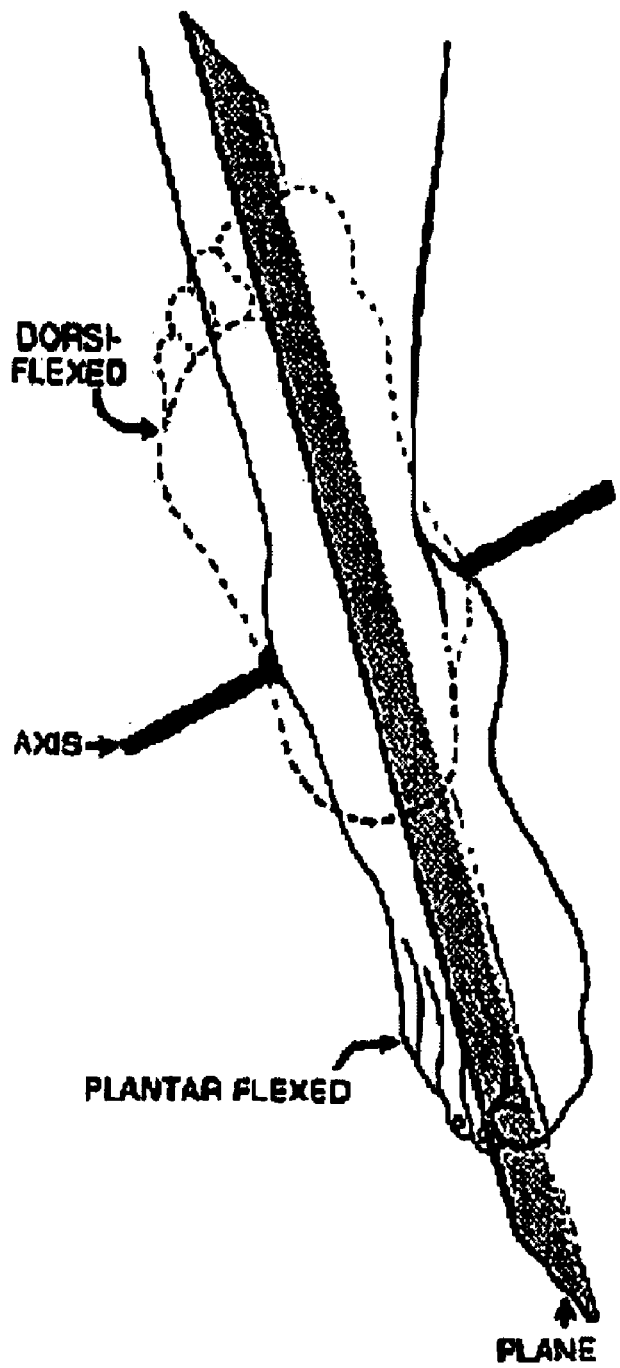
FIG. 2 is a depiction of the foot motion that results from rotation around the functional axis of the talocrural joint (TCJ), assuming that the leg remains in a fixed position.
Figure 3:
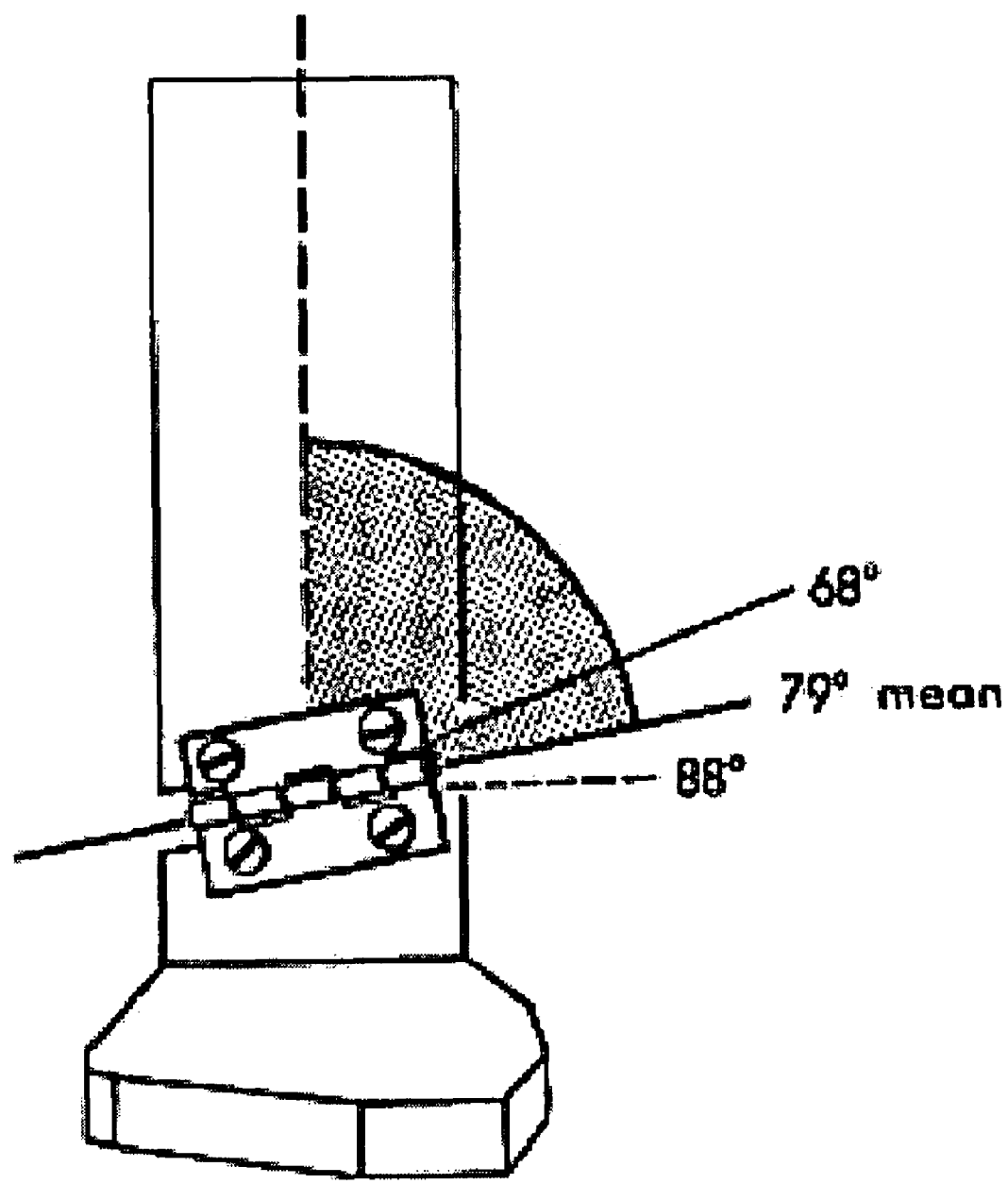
FIG. 3 is an illustration of a wooden model of the leg and foot segments, which are connected by an obliquely oriented hinge that approximates the orientation of the talocrural joint (TCJ) functional axis.
Figure 4:
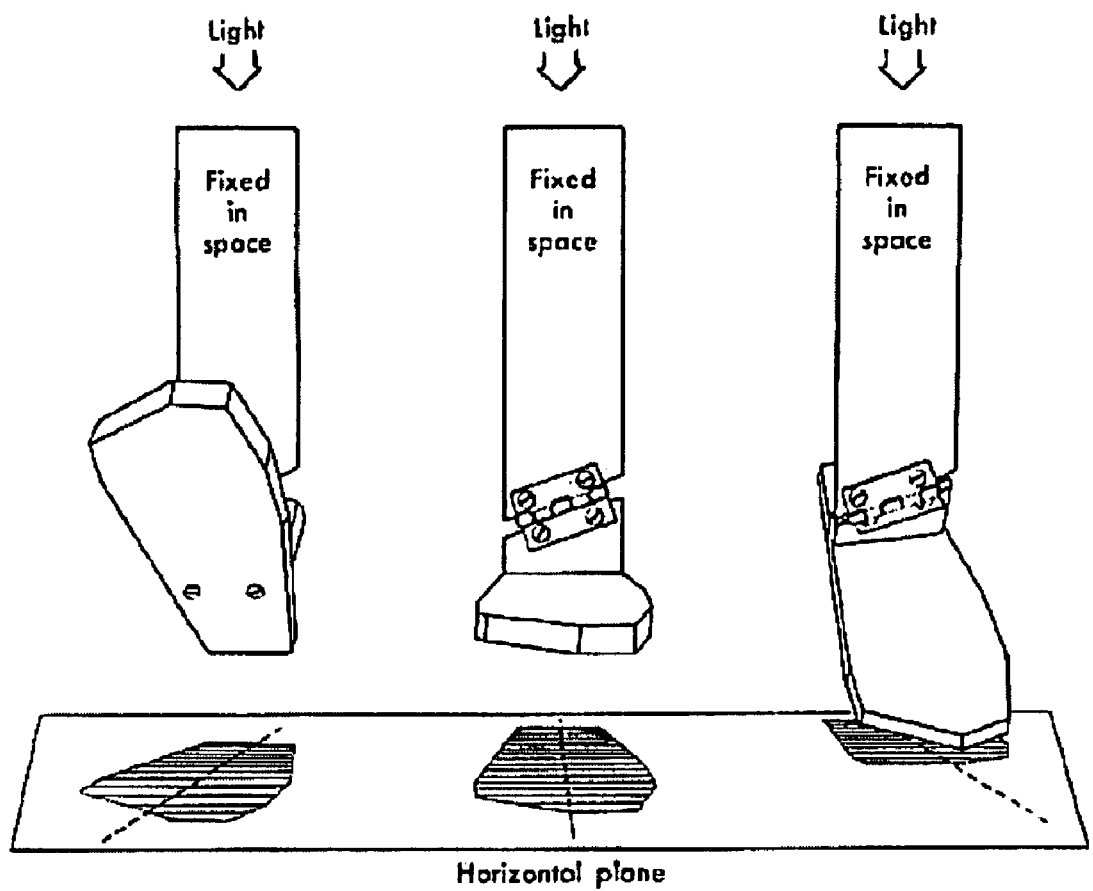
FIG. 4 is a depiction of the combined foot motions of dorsiflexion, pronation, and abduction that result from upward rotation around the talocrural joint (TCJ) functional axis, and the combined foot motions of plantar flexion, supination, and adduction that result from downward rotation around the talocrural joint (TCJ) functional axis.
Figure 5:
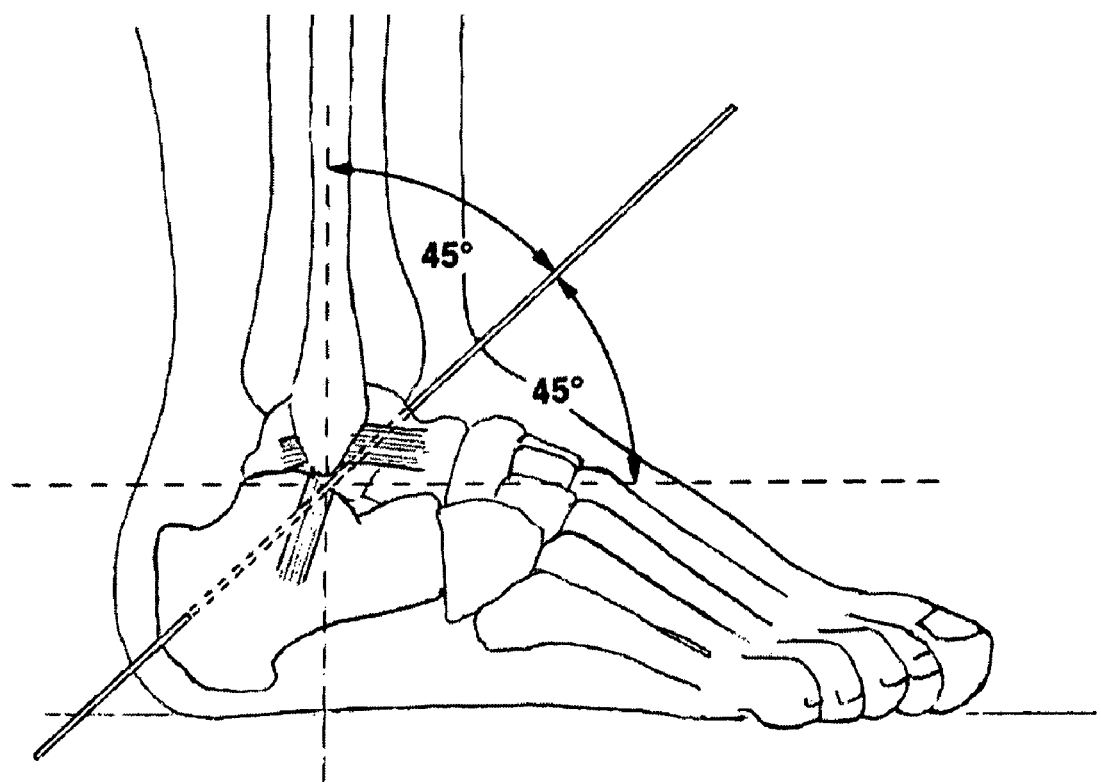
FIG. 5 is a depiction of the approximate 45-degree orientation of the functional axis of the subtalar joint (STJ) in the sagittal plane.
Figure 6:
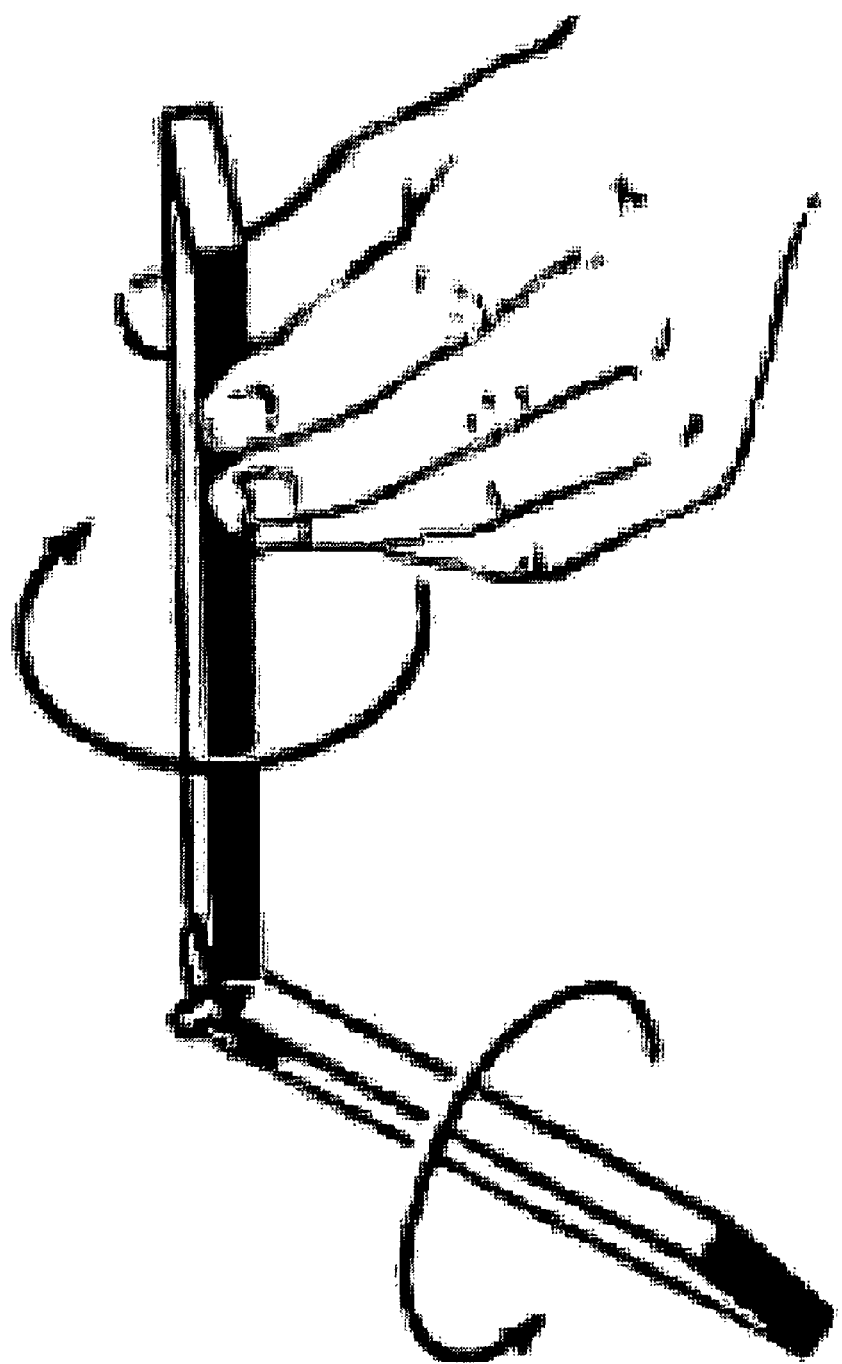
FIG. 6 is a depiction of a wooden model of the leg and foot segments, which are connected by a 45-degree mitred hinge that approximates the orientation of the subtalar joint (STJ) functional axis, and the opposite directions of rotation of the two segments that are produced by motion around the hinge.
Figure 7:
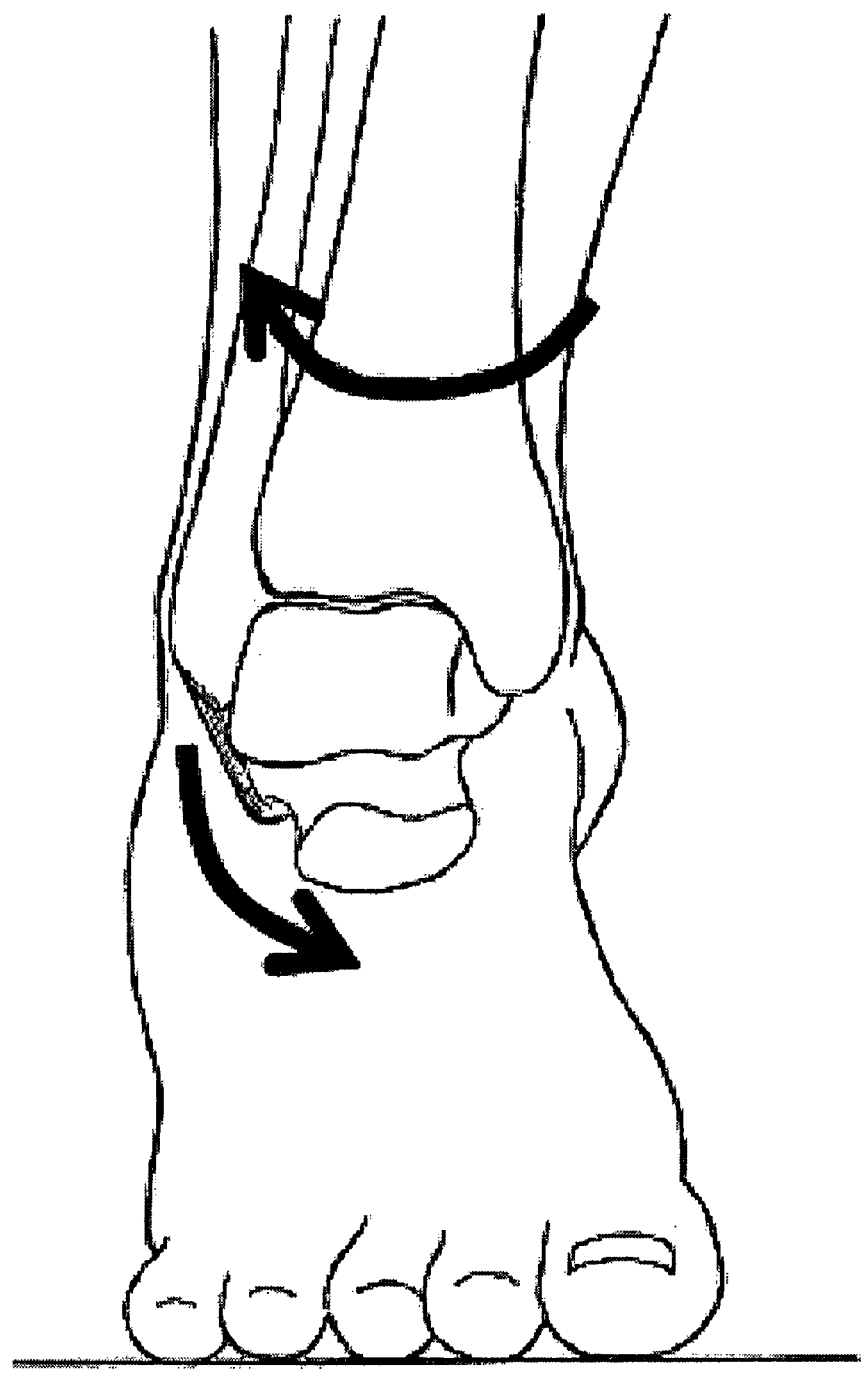
FIG. 7 is a depiction of simultaneous subtalar inversion and external rotation of the leg that results from rotation around the functional axis of the subtalar joint (STJ), which subjects the anterior talofibular ligament to tensile stress and tends to induce anterior translatory displacement of the talus from its normal position with the talocrural joint (TCJ).
Figure 8:
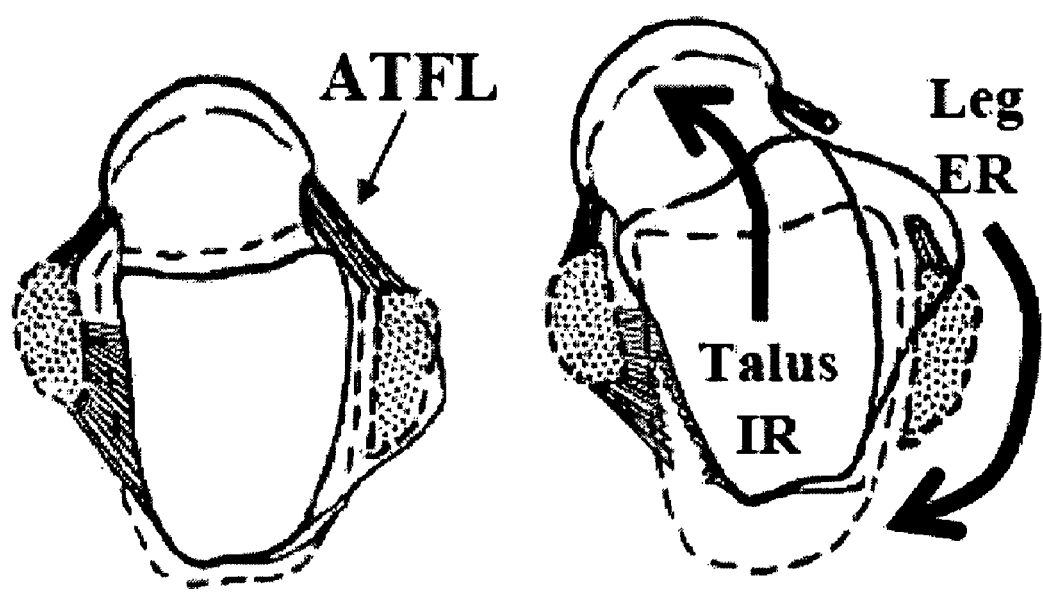
FIG. 8 is a depiction of a normal anatomical relationship between the talus, tibia, and fibula in the transverse plane (i.e., viewed from above, with an intact anterior talofibular ligament) and a depiction of the abnormal translatory and rotary displacement of the talus that results from a combination of leg external rotation and subtalar inversion when the anterior talofibular ligament is disrupted.
Figure 9:
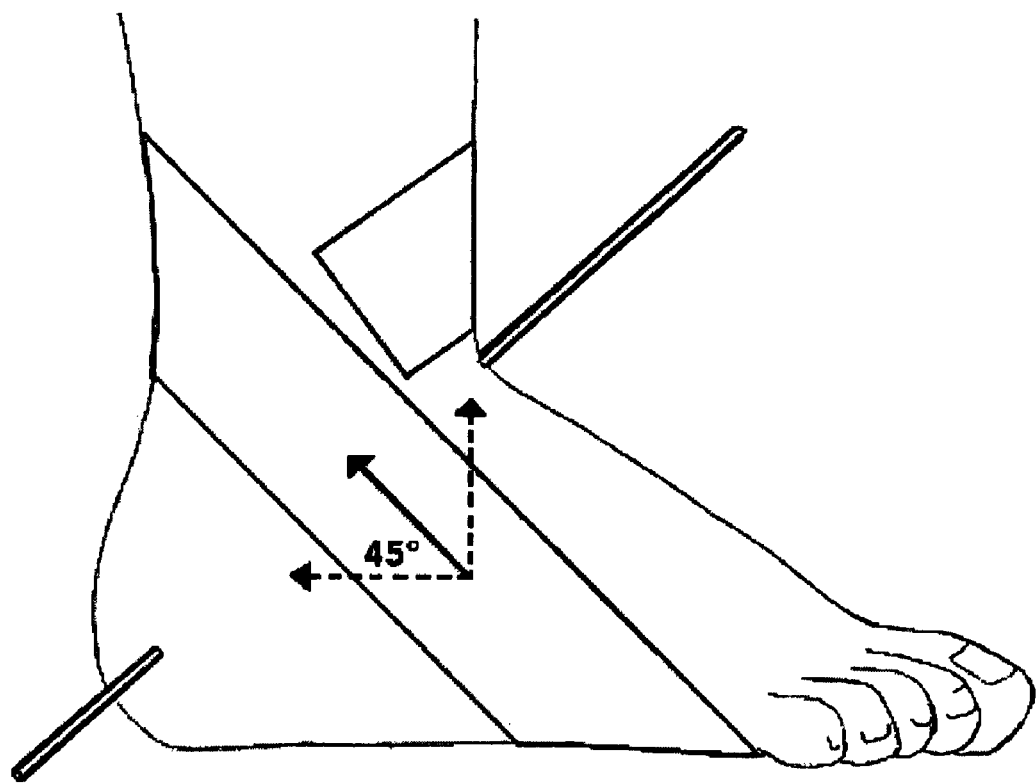
FIG. 9 is a depiction of the "subtalar sling" ankle taping procedure that has been shown effective for restriction of subtalar motion and restraint of translatory displacement of the talus.
Figure 10:
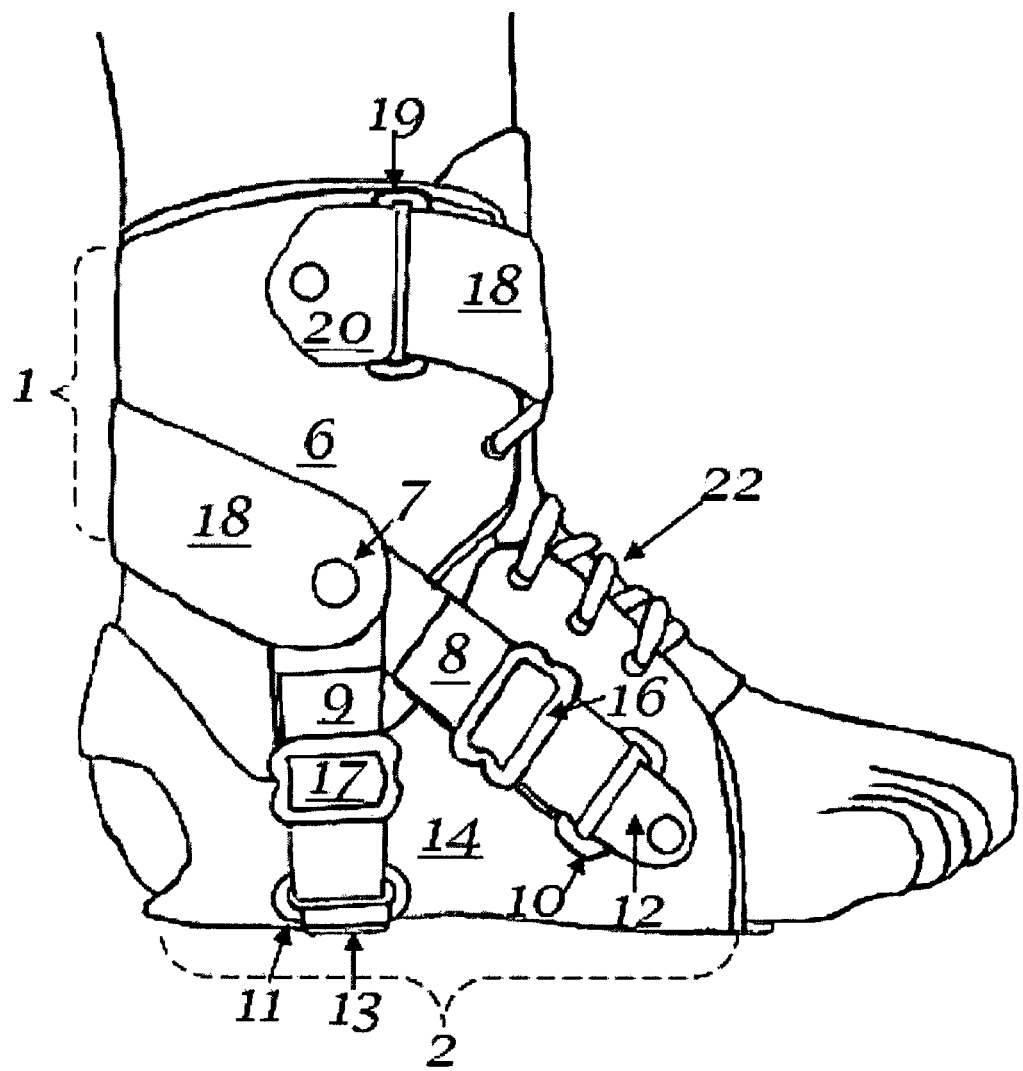
FIG. 10 is a lateral (outer) side view of the invention worn on a right ankle.
Figure 11:
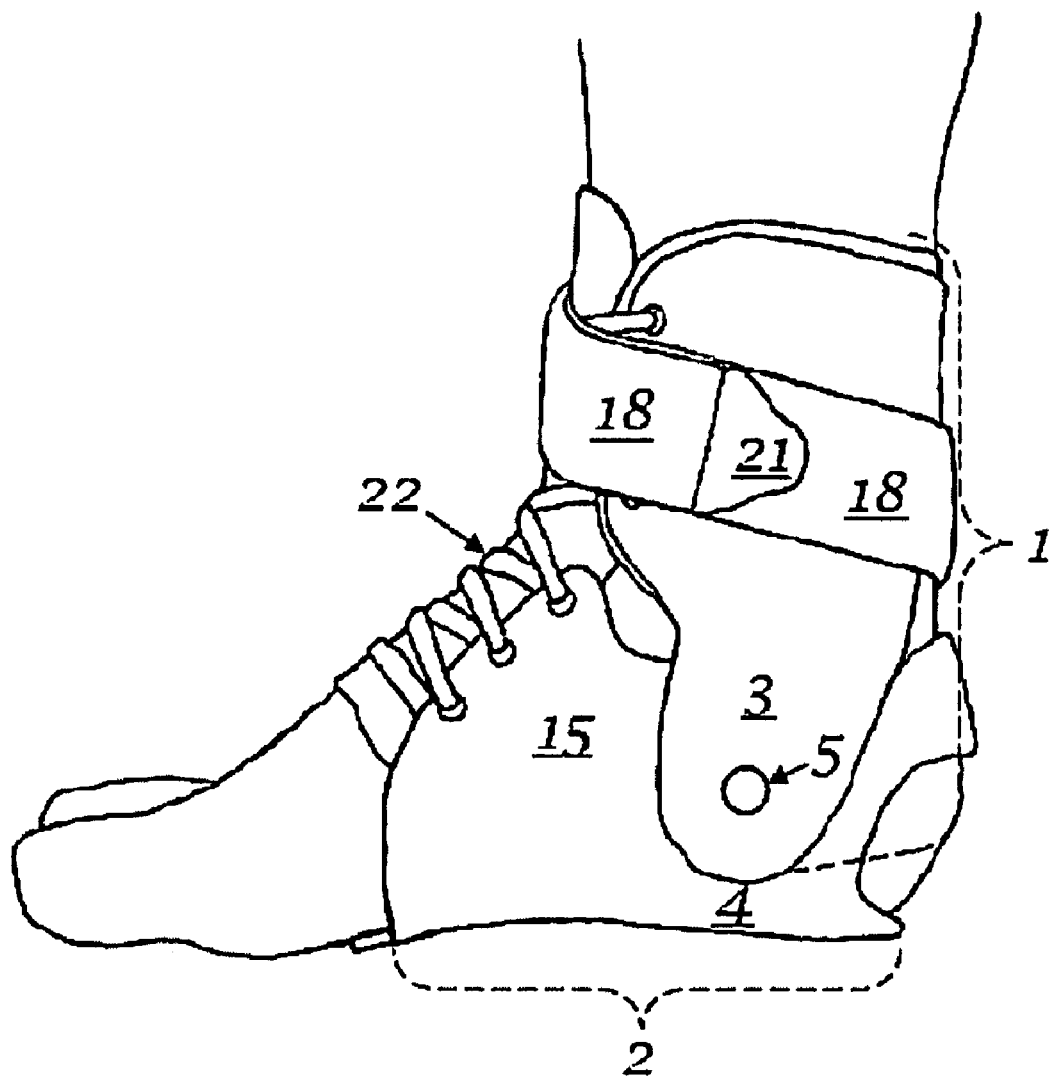
FIG. 11 is a medial (inner) side view of the invention worn on a right ankle.

The present invention is an ankle support system that incorporates the concept of forefoot to leg linkage, which has been demonstrated to be an effective ankle taping procedure for stabilization of the STJ and for restraint of translatory/rotary displacement of the talus in the transverse plane. The "subtalar sling" ankle taping procedure involves the application of semi-elastic strips of tape to the plantar aspect (sole) of the forefoot that are wrapped around the lateral border of the foot at an orientation of approximately 45 degrees and wrapped around the posterior, medial, and anterior aspects of the leg (Wilkerson, 2002, 2005; FIG. 9). If an oblique tether strap is anchored on the plantar surface of the forefoot portion of an orthosis, development of tension within the strap generates pressure against the foot in the same manner that oblique tape strips can produce uncomfortable pressure that is concentrated on the lateral border of the forefoot. The present invention incorporates an anchor point for an oblique tether strap to the foot component that is located on a lateral side panel, which distributes pressure over a broad area of the foot. The upper component 1 and 101 of the orthosis consists of a semi-rigid cuff that encircles approximately three-fourths of the lower leg (leaving either the anterior portion or the posterior portion of leg uncovered by the rigid cuff, and the uncovered area spanned by a closure strap). The lower component 2 and 102 may also be configured as a semi-rigid cuff that encircles approximately three-fourths of the foot segment (FIGS. 10-13), or it may be configured to resemble a semi-rigid foot orthotic (FIGS. 14-17). A downward projection or medial side portion 3 and 103 of upper component 1 and 101 and an upward projection 4 and 104 of the lower component overlap on one side of the ankle at a pivoting connection or pivot point 5 and 105, which provides a rigid "spacer bar" effect that resists compressive force. The leg component or upper component 1 and 101 and foot component or lower component 2 and 102 are also linked to one another on the opposite side by pivoting "tether strap" connections that have oblique 8 and 108 and vertical 9 and 109 orientations.

One embodiment incorporates pivoting tether straps 8 and 9, a pivoting derotation strap 18, and a first fastening means such as lace-up closure mechanism 22 that joins the lateral (outer) side portion 14 to the medial (inner) side portion 15 of the foot cuff or lower component 2, as well as the upper component lateral side portion 6 to the medial side portion 3 of the leg cuff or upper component 1 (FIGS. 10-13). This lace-up design offers the advantage of conformability of the leg and foot components to wide variability in foot size and leg circumference. The material used to construct the leg and foot components must be sufficiently pliable to allow for conformation to individual variability in foot and leg surface contours, but it must also be sufficiently rigid to resist distortion at the anchor points of the tether straps and the derotation strap. Alternatively, a second embodiment that is constructed from a more rigid material incorporates a derotation strap closure mechanism 118 on the back of the leg component or upper component 101, and pivoting oblique and vertical tether straps 108 and 109 that are attached to a foot orthotic component or lower component 102 (FIGS. 14-17). The lateral (outer) side portion 114 of foot component or lower component 102 is secured to the wearer's foot by means of a strap 123, which is anchored to the medial (inner) side portion of the foot component or lower component 102 by a pivoting rivet connection 126. Tension in strap 123 is generated by passage through D-ring 124, which is anchored to foot component or lower component lateral side portion 114 by mounting tab and rivet 125, and tension is maintained by a Velcro® hook and loop mechanism 135 at the end of strap 123. Greater rigidity of the foot and leg components enhances the stabilizing effect provided by the orthosis, but provides considerably less accommodation for individual variations in the size and shape of the extremity. Customized fabrication of the more rigid foot and leg components of the second embodiment to match the contours of an individual's extremity could optimize both comfort and restraint of abnormal joint displacements.

Figure 12:
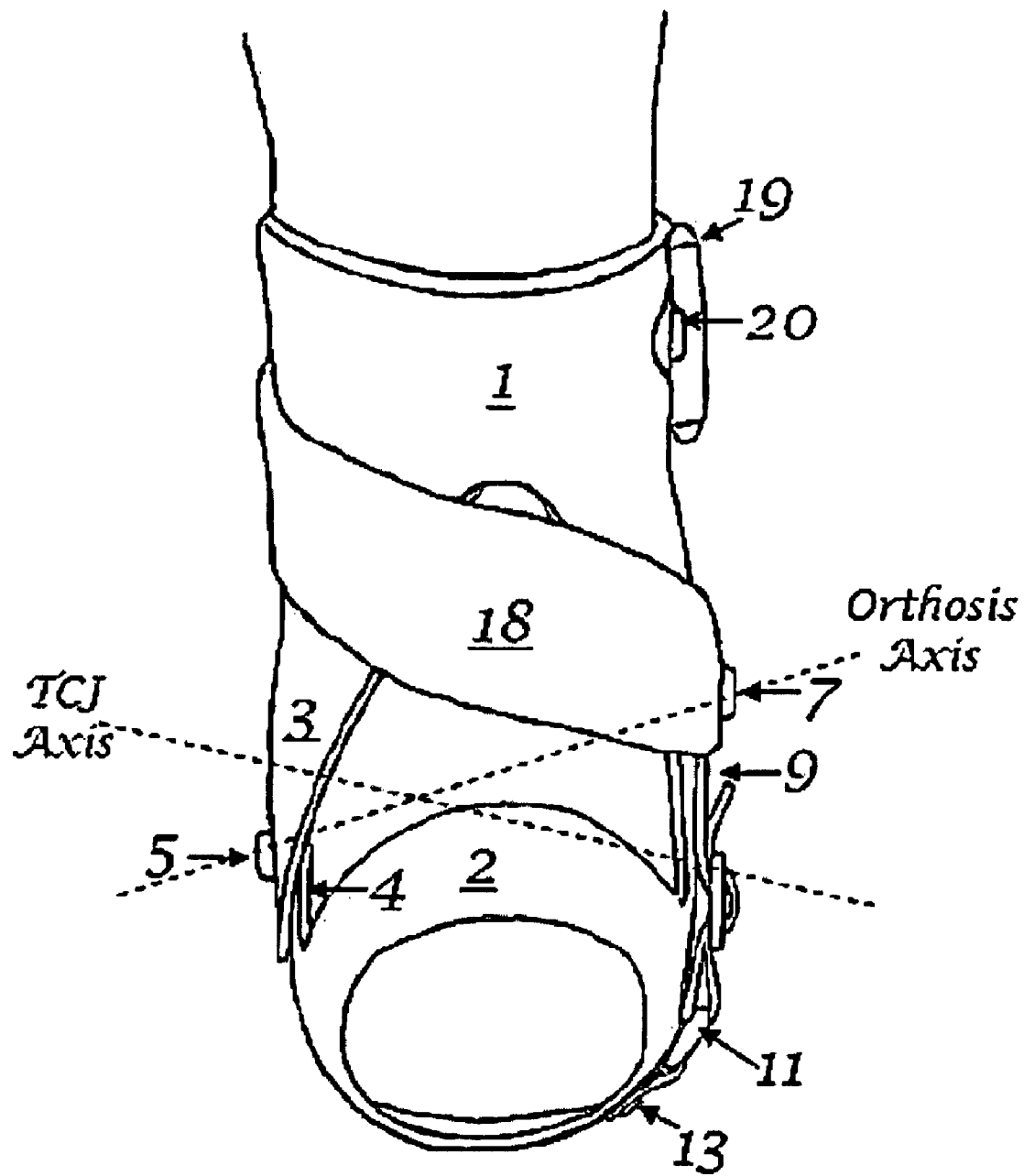
FIG. 12 is a posterior (rear) view of the invention worn on a right ankle, which includes depiction of the differing orientations of the functional axis of the talocural joint (TCJ) and the axis of rotation created by the positions of the orthosis pivot points in the frontal plane.
Figure 16:
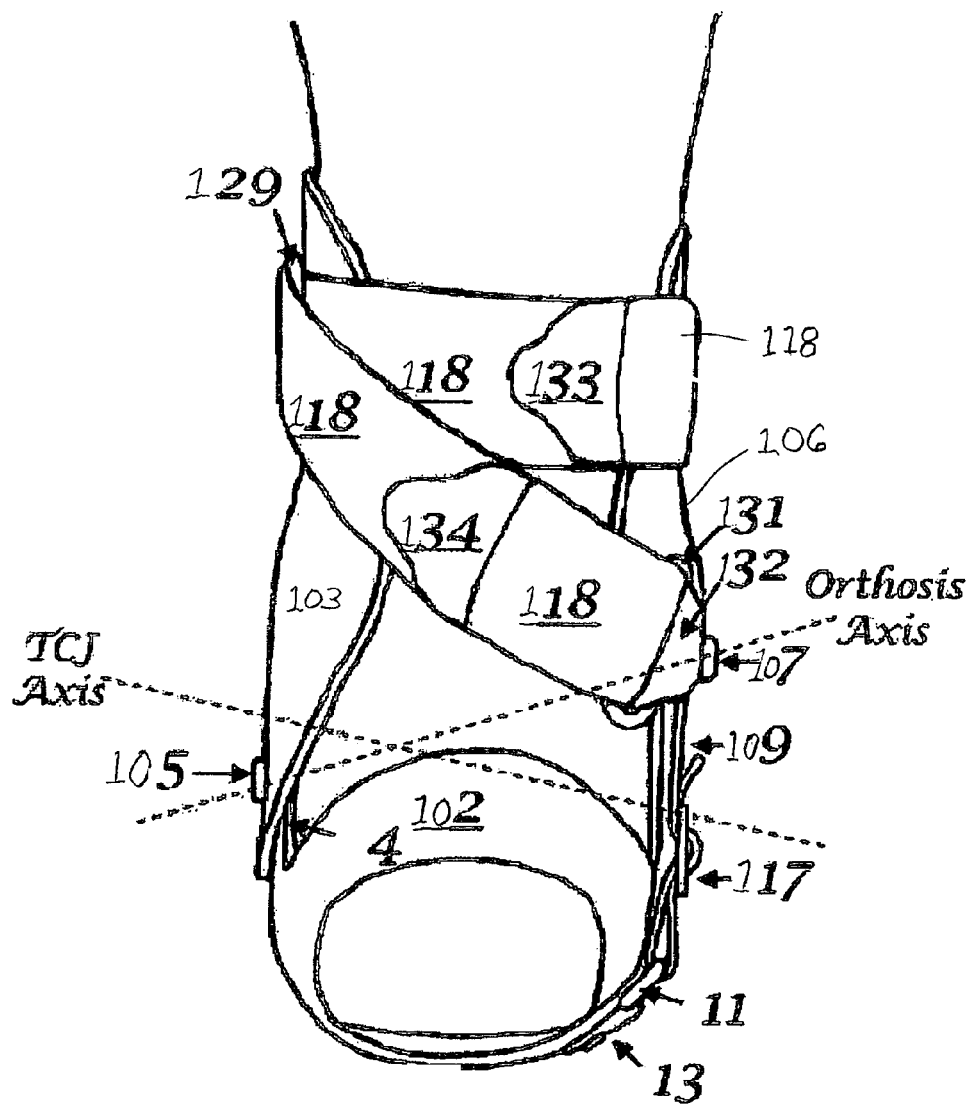
FIG. 16 is a posterior (rear) view of a second embodiment of the invention worn on a right ankle, which includes depiction of the differing orientations of the functional axis of the talocural joint (TCJ) and the axis of rotation created by the positions of the orthosis pivot points in the frontal plane.
Figure 18:
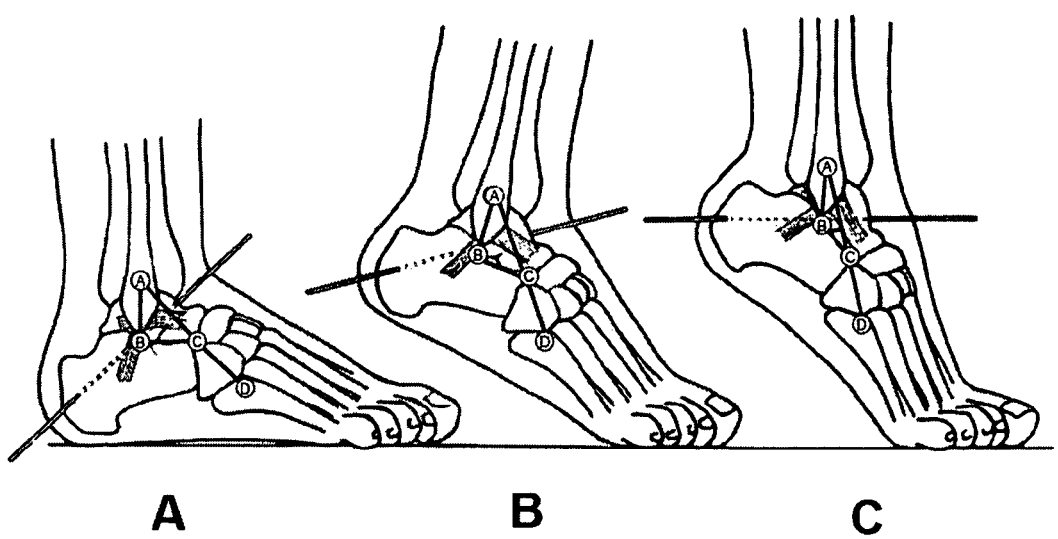
FIG. 18 is a depiction of change in the spatial relationships between the orthosis axis of motion (Point A), the talocrural joint (TCJ) functional axis of motion (Point B), the anterior margin of the subtalar joint (Point C), and the base of the fifth metatarsal (Point D), with Line A-D representing the orientation of the oblique tether strap, as the position of the TCJ moves from a neutral position (FIG. 18A) to plantar flexion (FIG. 18C).

The precise orientation of the oblique tether strap 8 and 108 in relation to the functional axes of the TCJ and the STJ is a critical factor influencing the effectiveness of the articulated ankle orthosis. To define its orientation, the ankle is assumed to be in a neutral position (i.e., long axis of the foot horizontal and long axis of the leg vertical) and viewed in the sagittal plane (i.e., looking at the lateral aspect). With the ankle in a neutral position, the axis of the subtalar joint is oriented at approximately 45 degrees relative to the long axes of both the foot and the leg in the sagittal plane. Because maximum resistance to inward rotation of the foot around the subtalar axis is provided by a line of force that is perpendicular to the axis, the orientation of the tether strap is also 45 degrees when the ankle is in a neutral position. The angle between the subtalar axis and the long axis of the leg increases when the ankle is plantar flexed (TCJ motion; FIG. 18). For a relatively perpendicular relationship to be maintained between the orientation of the oblique tether strap's line of force and the STJ axis, the point of attachment or pivoting anchoring point 7 and 107 of the tether strap 8 and 108 to the side panel or upper component lateral side portion 6 and 106 of the semi-rigid leg component of the orthosis must pivot, as well as the overlapping connection of the leg component or upper component 1 and 101 and foot component or lower component 2 and 102 at pivot point or rivet 5 and 105. The relative positions of the orthosis pivot points 5, 105 and pivoting anchoring point 7, 107 determine the orientation of the axis of orthosis rotation. Placement of the lateral pivot point or pivoting anchoring point 7 and 107 at a level that is higher than the placement of medial pivot point 5 and 105 creates an orthosis axis that is inclined in a direction that is opposite to the inclination of the functional axis of the TCJ in the frontal plane (FIGS. 12 and 16). Placement of the lateral pivot point or pivoting anchoring point 7 and 107 at position that is slightly more anterior (further forward) than medial pivot point 5 and 105 creates an orthosis axis that is opposite to the inclination of the TCJ axis in the transverse plane. The result is orthosis guidance of foot motion during plantar flexion that is coupled with pronation and abduction (outward movement of the foot), rather than supination and adduction (inward movement of the foot) that are coupled with plantar flexion during normal unrestrained TCJ motion.

Figure 13:
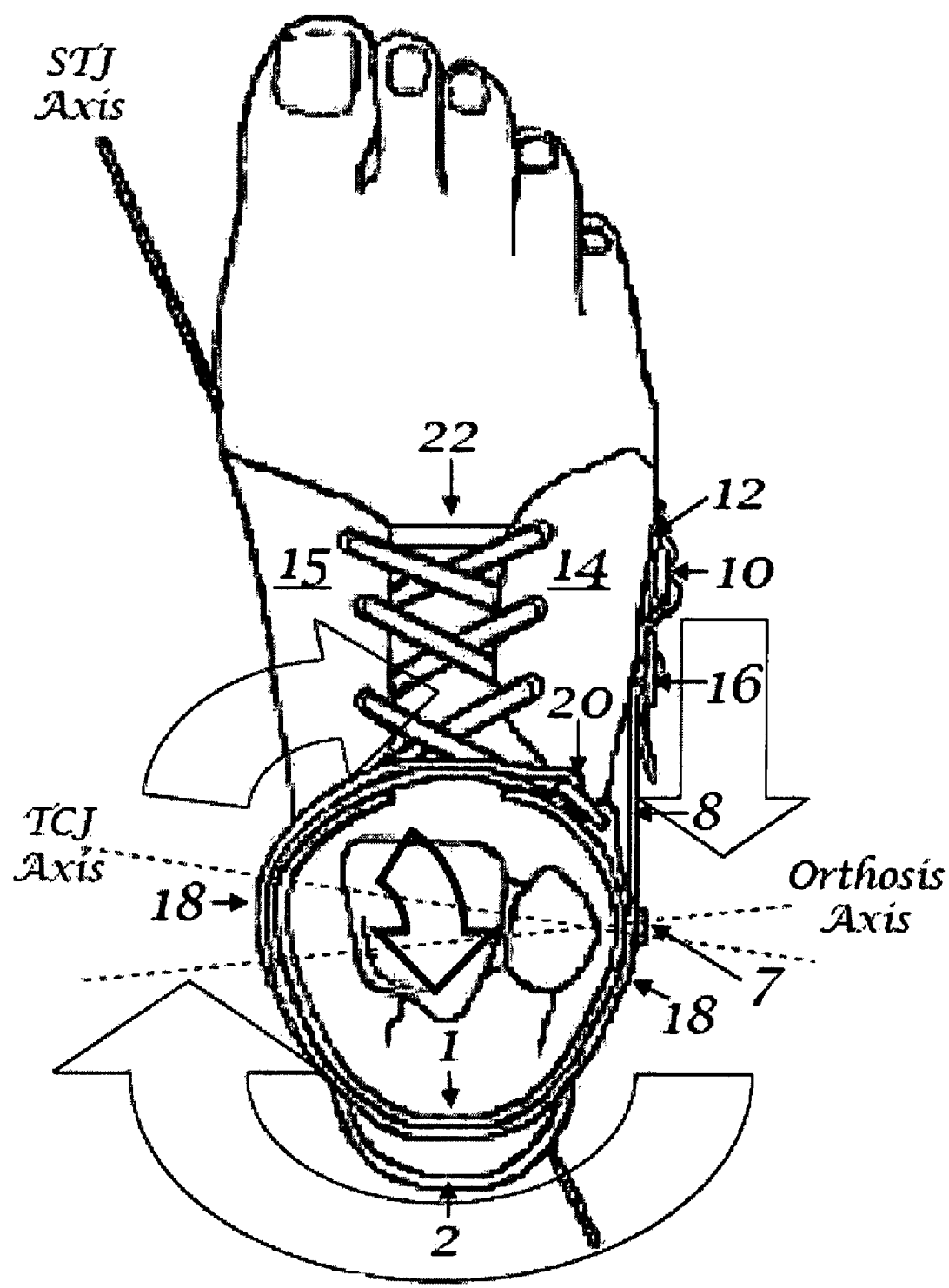
FIG. 13 is a superior (above) view of the invention worn of a right ankle, which includes depiction of the differing orientations of the functional axis of the talocural joint (TCJ) and the axis of rotation created by the positions of the orthosis pivot points in the transverse plane, as well as depiction of the stabilizing effect provided by the pivoting oblique tether strap and derotation strap system on the foot that counteracts leg external rotation torque and anterolateral rotary displacement of the talus.
Figure 14:
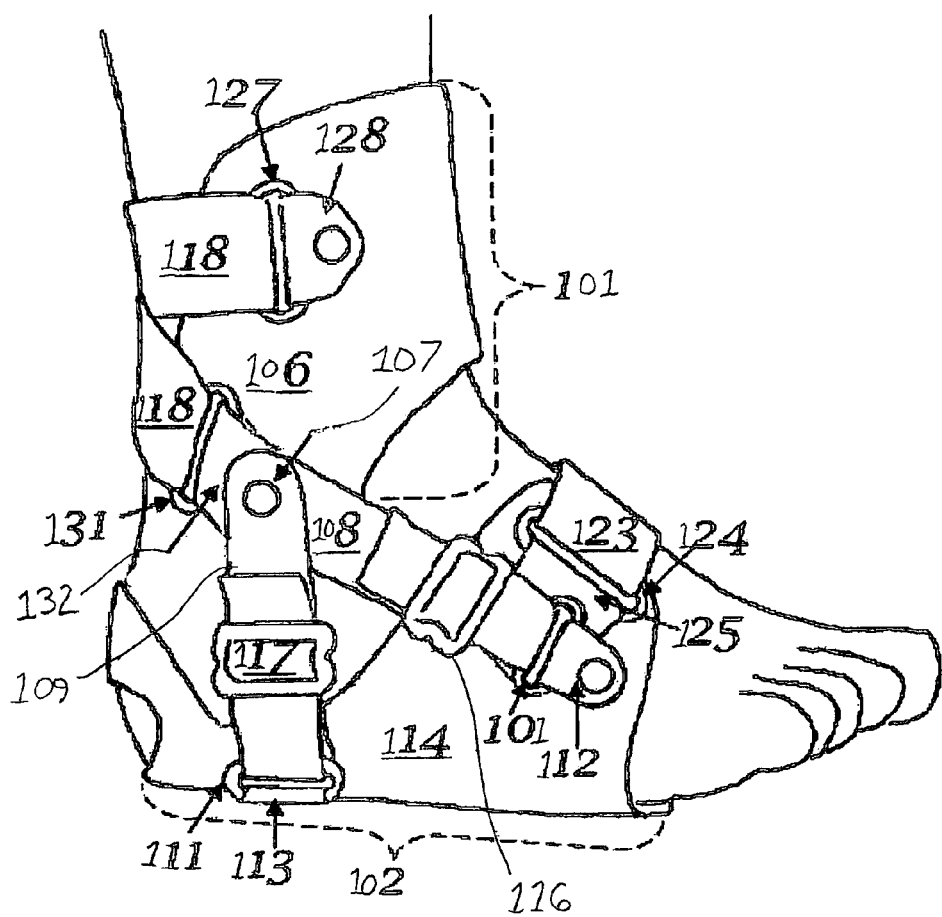
FIG. 14 is a lateral (outer) side view of a second embodiment of the invention worn on a right ankle.
Figure 15:
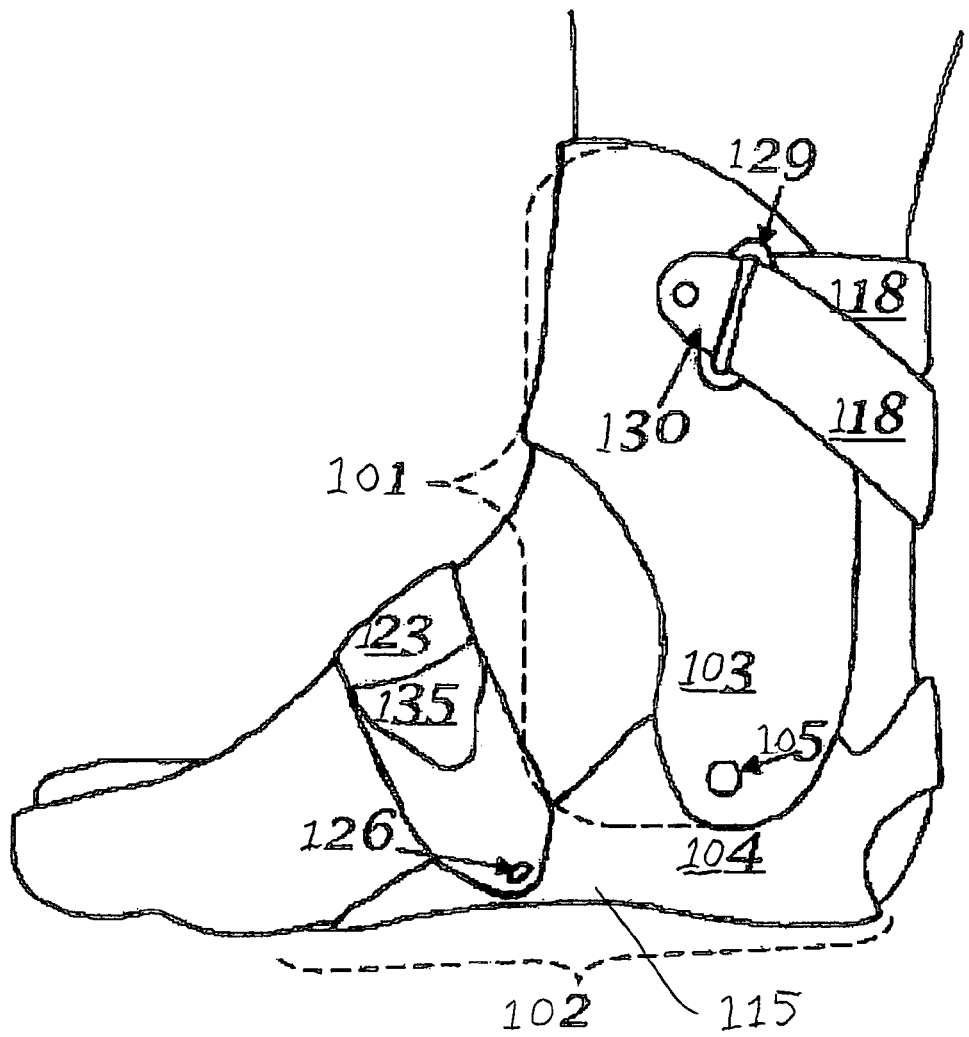
FIG. 15 a medial (inner) side view of a second embodiment of the invention worn on a right ankle.
Figure 17:
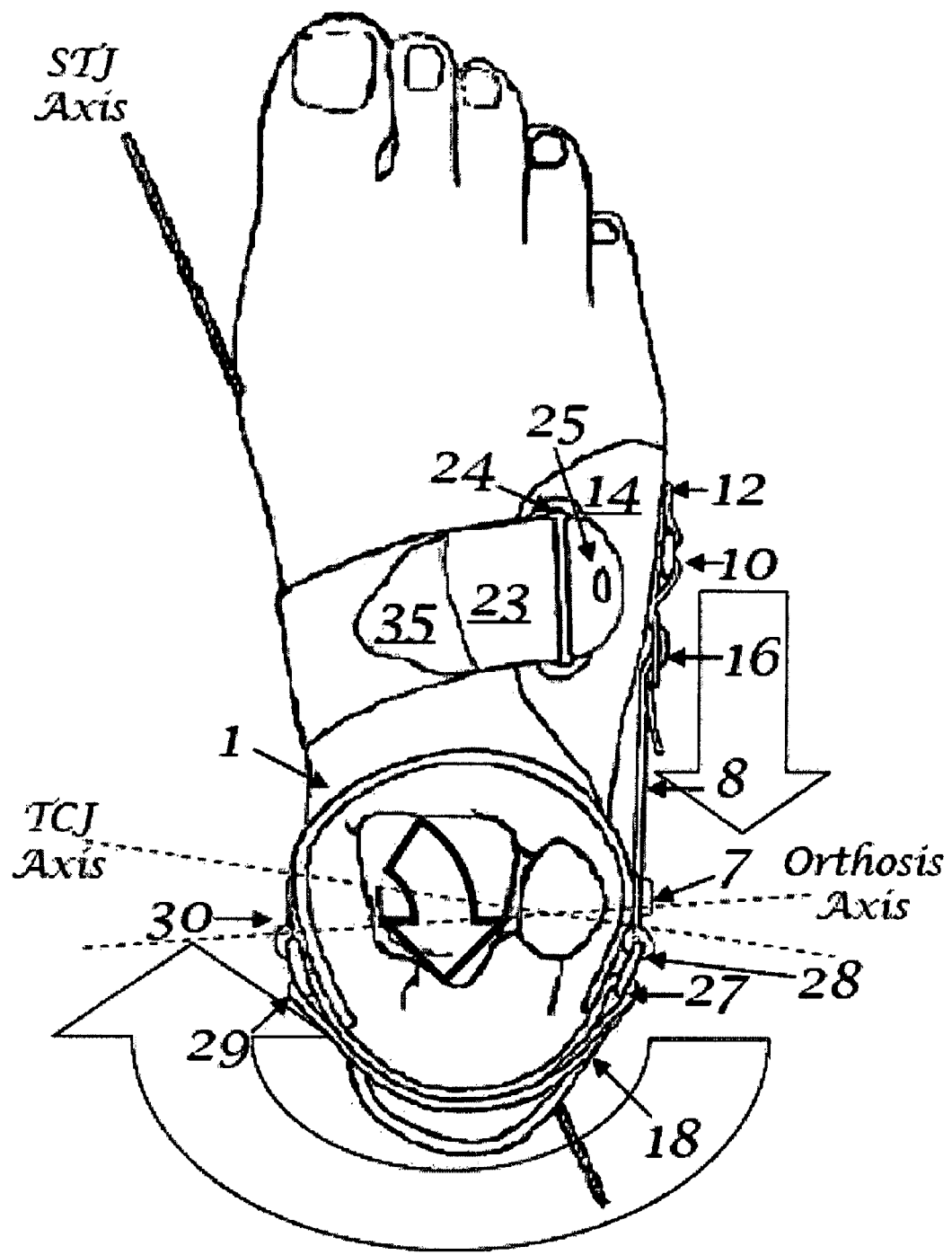
FIG. 17 is a superior (above) view of a second embodiment of the invention worn of a right ankle, which includes depiction of the differing orientations of the functional axis of the talocural joint (TCJ) and the axis of rotation created by the positions of the orthosis pivot points in the transverse plane, as well as depiction of the stabilizing effect provided by the pivoting oblique tether strap and derotation strap system on the foot that counteracts leg external rotation torque and anterolateral rotary displacement of the talus.

Strategic positioning of the attachment points such as pivoting anchoring point 107 and rivet 12, 112 of the pivoting oblique tether strap 8 and 108 in relation to the orientations of both the TCJ and STJ axes achieves several interrelated functions: 1) relatively unrestricted plantar flexion and dorsiflexion of the TCJ within the sagittal plane, 2) maintenance of an approximately perpendicular relationship between the longitudinal axis of the oblique tether strap 8 and 108 and the position of the STJ axis throughout the range of plantar flexion and dorsiflexion, and 3) increased tension development within the oblique tether strap 8 and 108 as the foot moves toward a greater degree of plantar flexion (FIG. 18). Because the axis of orthosis rotation (Point A) is located higher than the position of the functional axis of the TCJ (Point B), plantar flexion imposes tension on the oblique tether strap 8 and 108 (corresponding to Line A-D in FIG. 18) that would cause elongation if it were comprised of an elastic material. The non-elastic oblique tether strap 8 and 108 thereby functions like an external ligament that resists distraction of the joints that it spans (note that point B moves closer to Line A-C as the foot moves toward plantar flexion). Because either foot inversion or leg external rotation increases tension on the tether strap 8 and 108 and the contiguous derotation strap 18 and 118, the orthosis will provide resistance to abnormal translatory and rotary motion within the TCJ (FIGS. 13 and 17). A vertically-oriented tether strap 9 and 109 that pivots at the same location, pivoting anchoring point 7 and 107, as the oblique tether strap 8 and 108 provides protection for the calcaneofibular ligament.

Tension in oblique tether strap 8 and 108 is maintained and adjusted by a mechanism that includes D-ring 10 and 110, a mounting tab and rivet 12 and 112 that is attached to foot component side panel or lower component lateral side portion 14 and 114, and a double-slot buckle 16 and 116. An identical mechanism for vertical tether strap 9 and 109 includes D-ring 11 and 111, a mounting tab and rivet 13 and 113 that is attached to foot component side panel or lower component lateral side portion 14 and 114, and a double-slot buckle 17 and 117. For the embodiment depicted in FIGS. 10 through 13, derotation strap 18 is wrapped around the posterior, medial, and anterior aspects of the leg component or upper component 1, passed through D-ring 19 that is anchored to the lateral side panel or upper component lateral side portion 6 of the leg component by mounting tab and rivet 20, wrapped back upon itself under tension in an opposite anterior and medial direction, and secured by means of a Velcro® tab 21 at the end of the strap. The combination of tension in oblique tether strap 8 and derotation strap 18, which have common pivoting anchoring point 7, produces torque that opposes leg external rotation, subtalar inversion, and anterolateral rotary displacement of the TCJ (FIG. 13). For the embodiment depicted in FIGS. 14 through 17, derotation strap 118 provides the same effects as those described in the preceding text, but also provides a closure mechanism for the leg cuff component that firmly secures it to the leg of the wearer. A Velcro® tab 133 at one end of derotation strap 118 is first passed through D-ring 127, which is attached to lateral side panel or upper component lateral side portion 106 of the leg cuff component by mounting tab and rivet 128, and then attached to derotation strap 118. A Velcro® tab 134 at the opposite end of strap 118 is passed through D-ring 129, which is attached to medial side portion or panel 103 of the leg cuff component by means of mounting tab and rivet 130. After passage of strap 118 through D-ring 129, the course of the strap is changed from a lateral to medial horizontal orientation to a medial to lateral oblique orientation. Velcro® tab 134 and derotation strap 118 are then passed through D-ring 131, which is attached to the upper component lateral side portion 106 of the leg cuff component by means of mounting tab 132 and pivoting anchoring point or rivet 107 (which is also the anchor point for oblique tether strap 8). The end of derotation strap 118 is pulled back in an oblique lateral to medial direction to generate tension that simultaneously draws together the upper component lateral side portion 106 and medial side portion 103 of the leg cuff or upper component and generates torque that opposes leg external rotation, subtalar inversion, and anterolateral rotary displacement of the TCJ (FIG. 17). Derotation strap 118 tension is maintained by Velcro® tab 134.

The mechanism described for control of the combination of subtalar inversion and leg external rotation can also be applied for control of the combination of subtalar eversion and leg internal rotation by reversing the locations of the previously described lateral (outer) and medial (inner) orthosis components. In the context of chronic overuse injuries affecting the foot and leg, the term "pronation" is synonymous with excessive subtalar eversion. To control pronation, which is coupled with internal rotation of the leg, the disclosed subtalar stabilization mechanism would incorporate the following: 1) oblique and vertical tether straps 8, 108 and 9, 109, and their associated anchoring and tension adjustment components, on the medial (inner) aspect, 2) a derotation strap 18 and 118 that shares a pivoting anchoring point 7 and 107 with the tether straps 8, 108 and 9, 109 on the medial (inner) aspect and that wraps behind the leg in a medial to lateral direction, and 3) overlapped leg and foot side panel components that are connected by a pivot point 5 and 105 on the lateral aspect of the orthosis. Reversal of the relative locations of the medial and lateral orthosis components causes the relocated pivot points 5, 105 and pivoting anchoring point 7, 107 to closely approximate the orientation of the functional axis of the TCJ in the frontal and transverse planes. Control of excessive subtalar eversion and leg internal rotation is also a primary consideration for prevention of the "syndesomotic" ankle sprain, which most commonly occurs during participation in contact sports. Because participants in contact sports may be susceptible to ankle injury from either excessive subtalar inversion (and leg external rotation) or excessive subtalar eversion (and leg internal rotation), oppositely oriented oblique tether straps 8 and 108 and derotation straps 18 and 108 are necessary on both the lateral and medial sides of the orthosis, and the leg and foot components must have overlapping side panels and pivot joint connections on both the medial and lateral sides. Such an embodiment replaces the vertically oriented tether strap 9 and 109 with an upward side panel extension of the foot component's semi-rigid structure, which overlaps the semi-rigid structure of the leg component, and is secured to the leg component side panel by a pivoting rivet connection, which also serves a the common anchor point for the oblique tether strap 8 and 108 and derotation strap 18 and 118. This bilateral incorporation of pivot joint connections between the leg cuff component and foot cuff/orthotic component and the bilateral incorporation of oblique tether straps and derotation straps requires both pivot joints to fulfill the functions of both pivot point 5 and 105 and pivoting anchoring point 7 and 107. For the oblique tether straps 8 and 108 to be oriented in a manner that is approximately perpendicular to the orientation of the functional axis of the STJ in the sagittal plane on both sides of the orthosis, the combined orthosis pivot points 5 and 105 and pivoting strap-anchoring points 7 and 107 must be positioned at approximately the same height, which creates an orthosis axis of rotation that is relatively horizontal in the frontal plane.

In summary, the key to ankle stabilization for prevention of lateral ligament injury is restriction of excessive forefoot inversion and leg ER. The most effective means of controlling STJ motion is achieved through a pivoting forefoot to leg linkage. Because the most common mechanism of ankle injury is associated with lateral joint distraction, the lateral side of the ankle orthosis should have an adjustable "tether strap" that spans the lateral joints and functions like an external ankle ligament. Concomitant medial joint compression is resisted by the presence of a medial "spacer bar" element that is formed by the overlapped upper and lower semi-rigid orthosis components. Precise placement of moveable orthosis elements in relation to selected anatomical landmarks is essential for preservation of normal functional ankle motions, and for restraint of undesirable pathologic motions. Because external rotation of the leg increases tension in the contiguous derotation and oblique tether straps, a tensile force is applied to the lateral aspect of the foot that tends to lift it into an everted position. Thus, the derotation and oblique tether strap mechanism reverses the normal biomechanical coupling of leg external rotation and subtalar inversion. Precisely the same effect is produced if the mechanism is adapted to function on the medial side of the orthosis, i.e., internal rotation of the leg increases tension on the straps, which tends to lift the medial border of the foot. The disclosed ankle derotation and subtalar stabilization system offers greater advantages than any other that is presently available for the prevention and management of lateral ankle ligament injury, pronation-related overuse syndromes, and syndesmotic ankle injury, while presenting minimal interference to the efficient performance of athletic activities. The disclosed system can be readily incorporated into the structure of an ankle orthosis or the structure of athletic shoes or work/recreation boots.

What is claimed is:

1. An ankle orthosis comprising:
a lower component and a fastening means that completely encircles and substantially covers the plantar, lateral, dorsal, and medial aspects of the foot;
an upper component and the fastening means that completely encircles and substantially covers the anterior, lateral, posterior, and medial aspects of the leg;
a first non-elastic and adjustable-tension strap having a first end secured to and extending from an anchor point on a lateral surface of the forefoot portion of the lower component, said first strap extending obliquely across a lateral aspect of the foot and ankle, and secured at its second end to a first rivet on a lateral aspect of the upper component that is higher and more anterior than the normal position of the functional axis of the talocrural joint;
a second non-elastic and adjustable-tension strap having a first end secured to and extending from the first rivet used for the second end of the first strap on the lateral aspect of the upper component, said second strap passing behind the upper component and passing through a pivoting D-ring attached to the upper component, and said second non-elastic and adjustable tension strap having a second end secured by a hook and loop fastener tab;
a third non-elastic and adjustable-tension strap having a first end secured to and extending from an anchor point on a lateral aspect of the hindfoot portion of the lower component, said third strap extending vertically across the lateral aspect of the ankle and having a second end secured to the first rivet used for the second end of the first strap and the first end of the second strap on the lateral aspect of the upper component; and
a second rivet in overlapping medial side portions of the lower and upper components that pivots around a point that is lower and more posterior than the normal position of the functional axis of the talocrural joint.

2. The ankle orthosis of claim 1, wherein the first and third straps are located on a medial aspect of the orthosis, the first end of the second strap is located on the medial aspect of the orthosis, the first rivet is located on a medial aspect of the upper component at a point that approximates the location of the functional axis of the talocrural joint, and a second rivet is located adjacent to an overlapping junction of the side portions of the lower and upper components at a point that approximates the location of the functional axis of the talocrural joint.

3. The ankle orthosis of claim 1, wherein the first strap is replicated on both a medial aspect and a lateral aspect of the orthosis, the second strap is replicated with first ends anchored to a rivet on both the medial aspect and the lateral aspect of the orthosis and second ends passing through D-rings attached to opposite sides of the upper component, the third strap is replaced by an upward extension of the lateral side portion of the foot component, overlapping junctions between both the medial side portions of the lower and upper components and a lateral side portion of the lower and upper components that pivots on the medial aspect of the orthosis around a point that approximates the location of the functional axis of the talocrural joint and on the lateral aspect of the orthosis around a point that is higher and more anterior than the normal position of the functional axis of the talocrural joint, and the rivets serve as anchor points for the first straps and the second straps.

4. The ankle orthosis of claim 3, wherein the upper and lower components are integrated into a shoe.

5. The ankle orthosis of claim 1, wherein the upper and lower components are integrated into a shoe.

6. An ankle orthosis comprising:
(a) a lower component, said lower component being adapted to engage a user's foot;
(b) an upper component, said upper component being adapted to engage the user's lower leg;
(c) a first rivet, said first rivet being located adjacent to the lateral aspect of the user's ankle;
(d) a first strap, said first strap having a first strap first end that is connected to the lower component and a first strap second end that is connected to the first rivet;
(e) a second strap, said second strap having a second strap first end that is connected to the first rivet and a second strap second end that is removably connected to the upper component;
(f) a third strap, said third strap having a third strap first end that is connected to the lower component and a third strap second end that is connected to the first rivet;
(g) a second rivet, said second rivet being located in an overlapping area of the lower component and the upper component adjacent to the medial aspect of the user's ankle.

7. The ankle orthosis of claim 6 further comprising a second pivot point located in an overlapping area of the lower component and the upper component adjacent to the lateral aspect of the user's ankle.

8. The ankle orthosis of claim 6 further comprising:
(h) a fourth strap, said fourth strap having a fourth strap first end that is connected to the lower component and a fourth strap second end that is connected to the second rivet;
(i) a fifth strap, said fifth strap having a fifth strap first end that is connected to the second rivet and a fifth strap second end that is removably connected to the upper component;
(j) a sixth strap, said sixth strap having a sixth strap first end that is connected to the lower component and a sixth strap second end that is connected to the second rivet.

9. The ankle orthosis of claim 6 wherein the upper component encircles the user's lower leg.

10. The ankle orthosis of claim 6 wherein the upper component includes an opening.

11. The ankle orthosis of claim 6 wherein the lower component encircles the user's foot.

12. The ankle orthosis of claim 6 wherein the lower component includes an opening.

13. The ankle orthosis of claim 6 wherein the upper component includes a fastening means.

14. The ankle orthosis of claim 6 wherein the lower component includes a fastening means.

15. The ankle orthosis of claim 6 wherein the first strap second end is pivotally connected to the first rivet, second strap first end is pivotally connected to the first rivet, and third strap second end is pivotally connected to the first rivet.

16. The ankle orthosis of claim 6 wherein the first strap first end is fixedly connected to the lower component in an area adjacent to the user's forefoot.

17. The ankle orthosis of claim 6 wherein the third strap first end is fixedly connected to the lower component in an area adjacent to the user's heel and substantially parallel to the longitudinal axis of the user's leg.

18. The ankle orthosis of claim 6 wherein the upper component includes a fastening means adapted to securely engage the user's leg.

19. The ankle orthosis of claim 6 wherein the lower component includes a fastening means adapted to securely engage the user's foot.

20. Then ankle orthosis of claim 6 wherein the first rivet is located above and to the anterior of a functional axis of the user's talocrural joint and the second rivet is located below and to the posterior of the functional axis of the user's talocrural joint.

21. An ankle orthosis comprising:
(a) a lower component, said lower component being adapted to engage a user's foot;
(b) an upper component, said upper component being adapted to engage the user's lower leg;
(c) a first rivet, said first rivet being located adjacent to the medial aspect of the user's ankle;
(d) a first strap, said first strap having a first strap first end that is connected to the lower component and a first strap second end that is connected to the first rivet;
(e) a second strap, said second strap having a second strap first end that is connected to the first rivet and a second strap second end that is removably connected to the upper component;
(f) a third strap, said third strap having a third strap first end that is connected to the lower component and a third strap second end that is connected to the first rivet;
(g) a second rivet, said second rivet being located in an overlapping area of the lower component and the upper component adjacent to the lateral aspect of the user's ankle.

* * * * *